United States Patent [19]

Kast et al.

[11] Patent Number: 5,374,609
[45] Date of Patent: Dec. 20, 1994

[54] CYCLOHEXENONE OXIME ETHERS AND THEIR USE AS HERBICIDES

[75] Inventors: Juergen Kast, Boehl-Iggelheim; Norbert Meyer, Ladenburg; Ulf Misslitz, Neustadt; Albrecht Harreus, Ludwigshafen; Thomas Kuekenhoehner, Frankenthal; Harald Rang, Ludwigshafen; Matthias Gerber, Mutterstadt; Karl-Otto Westphalen, Speyer; Helmut Walter, Obrigheim, all of Germany

[73] Assignee: BASF Aktiengesellschaft, Ludwigshafen, Germany

[21] Appl. No.: 65,912

[22] Filed: May 25, 1993

Related U.S. Application Data

[62] Division of Ser. No. 697,058, May 8, 1991, Pat. No. 5,250,505.

[30] Foreign Application Priority Data

May 9, 1990 [DE] Germany .................... 4014984

[51] Int. Cl.$^5$ ................... A01N 33/24; C07C 251/50
[52] U.S. Cl. .................. 504/344; 564/256; 564/258
[58] Field of Search ............ 504/288, 292, 293, 344; 549/13, 14, 22, 30, 88, 417, 419, 426, 451; 564/256, 258; 514/640

[56] References Cited

U.S. PATENT DOCUMENTS 5,190,573  2/1993  Misslitz et al. .................... 504/292

Primary Examiner—Mukund J. Shah
Assistant Examiner—Y. N. Gupta
Attorney, Agent, or Firm—Keil & Weinkauf

[57] ABSTRACT

Cyclohexenone oxime ethers I

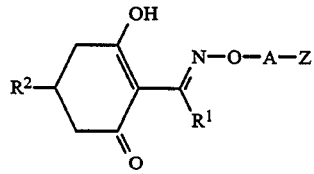

(I)

where $R^1$ is $C_1$–$C_6$-alkyl, A is unsubstituted or substituted $C_3$–$C_6$-alkynylene, Z is unsubstituted or substituted phenyl or a 5-membered or 6-membered heteroaromatic and $R^2$ is $C_1$–$C_4$-alkoxy-$C_1$–$C_6$-alkyl, $C_1$–$C_4$-alkylthio-$C_1$–$C_6$-alkyl, unsubstituted or substituted $C_3$–$C_7$-cycloalkyl or $C_5$–$C_7$-cycloalkenyl, an unsubstituted or substituted 5-membered saturated heterocyclic structure having one or two hetero atoms, an unsubstituted or substituted 6-membered or 7-membered saturated or monounsaturated or diunsaturated heterocyclic structure having one or two hetero atoms, an unsubstituted or substituted 5-membered heteroaromatic having one to three hetero atoms or unsubstituted or substituted phenyl or pyridyl, and their agriculturally useful salts and esters of $C_1$–$C_{10}$-carboxylic acids and inorganic acids, are suitable as herbicides.

3 Claims, No Drawings

CYCLOHEXENONE OXIME ETHERS AND THEIR USE AS HERBICIDES

This is a division of application Ser. No. 07/697,058, filed May 8, 1991 now U.S. Pat. No. 5,250,505.

The present invention relates to novel herbicidal cyclohexenone oxime ethers of the formula I

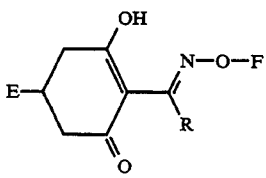

where
- $R^1$ is $C_1-C_6$-alkyl;
- A is a $C_3-C_6$-alkynylene chain which is unsubstituted or substituted by 1 to 3 $C_1-C_3$-alkyl groups or halogen atoms;
- Z is phenyl or a 5-membered or 6-membered heteroaromatic structure having one to three hetero atoms selected from the group consisting of three nitrogen atoms and one oxygen or sulfur atom, where the aromatic radicals may be unsubstituted or substituted by n identical or different radicals X;
- X is nitro, cyano, halogen, $C_1-C_4$-alkyl, $C_1-C_4$-alkoxy, $C_1-C_4$-alkylthio, $C_1-C_4$-haloalkyl, $C_1-C_4$-haloalkoxy, carboxyl, $C_1-C_4$-alkoxycarbonyl, benzyloxycarbonyl or phenyl, where the aromatic radicals may furthermore carry one to three substituents selected from the group consisting of nitro, cyano, halogen, $C_1-C_4$-alkyl, $C_1-C_4$-alkoxy, $C_1-C_4$-alkylthio, $C_1-C_4$-haloalkyl, $C_1-C_4$-haloalkoxy, carboxyl, $C_1-C_4$-alkoxycarbonyl and benzyloxycarbonyl;
- n is from 0 to 3, or from 1 to 5 where X is halogen, and $R^2$ is $C_1-C_4$-alkoxy-$C_1-C_6$-alkyl or $C_1-C_4$-alkylthio-$C_1-C_6$-alkyl;
- $C_3-C_7$-cycloalkyl or $C_5-C_7$-cycloalkenyl, where these groups may furthermore carry one to three radicals selected from the group consisting of $C_1-C_4$-alkyl, $C_1-C_4$-alkoxy, $C_1-C_4$-alkylthio, $C_1-C_4$-haloalkyl, hydroxyl and halogen;
- a 5-membered saturated heterocyclic structure which contains one or two hetero atoms selected from the group consisting of oxygen and sulfur and which may furthermore carry one to three radicals selected from the group consisting of $C_1-C_4$-alkyl, $C_1-C_4$-alkoxy, $C_1-C_4$-alkylthio and $C_1-C_4$-haloalkyl;
- a 6-membered or 7-membered saturated or monounsaturated or diunsaturated heterocyclic structure containing one or two hetero atoms selected from the group consisting of oxygen and sulfur, where the heterocyclic structure may furthermore carry one to three radicals selected from the group consisting of hydroxyl, halogen, $C_1-C_4$-alkyl, $C_1-C_4$-alkoxy, $C_1-C_4$-alkylthio and $C_1-C_4$-haloalkyl;
- a 5-membered heteroaromatic structure containing one to three hetero atoms selected from the group consisting of two nitrogen atoms and one oxygen or sulfur atom, where the heterocyclic structure may furthermore carry one to three radicals selected from the group consisting of halogen, cyano, $C_1-C_4$-alkyl, $C_1-C_4$-alkoxy, $C_1-C_4$-alkylthio, $C_1-C_4$-haloalkyl, $C_2-C_6$-alkenyl, $C_2-C_6$-alkenyloxy, $C_2-C_6$-haloalkenyl and $C_1-C_4$-alkoxy-$C_1-C_4$-alkyl, or phenyl or pyridyl, where these groups may furthermore carry one to three radicals selected from the group consisting of halogen, nitro, cyano, $C_1-C_4$-alkyl, $C_1-C_4$-alkoxy, $C_1-C_4$-alkylthio, $C_1-C_4$-haloalkyl, $C_3-C_6$-alkenyloxy, $C_3-C_6$-alkynyloxy and $-NR^3R^4$, where $R^3$ is hydrogen, $C_1-C_4$-alkyl, $C_3-C_6$-alkenyl or $C_3-C_6$-alkynyl and $R^4$ is hydrogen, $C_1-C_4$-alkyl, $C_3-C_6$-alkenyl, $C_3-C_6$-alkynyl, $C_1-C_6$-acyl or benzoyl, where the aromatic ring may additionally carry one to three substituents selected from the group consisting of nitro, cyano, halogen, $C_1-C_4$-alkyl, $C_1-C_4$-alkoxy, $C_1-C_4$-alkylthio and $C_1-C_4$-haloalkyl, and their agriculturally useful salts and esters of $C_1-C_{10}$-carboxylic acids and inorganic acids.

The present invention furthermore relates to a process and intermediates for their preparation and their use as crop protection agents.

The novel cyclohexenones I are evidently acidic, i.e. they can form simple reaction products such as salts of alkali metal or alkaline earth metal compounds or enol esters.

The compounds of the formula I can occur in a plurality of tautomeric forms, all of which are embraced by the claim.

The literature describes cyclohexenones of the general formula I′

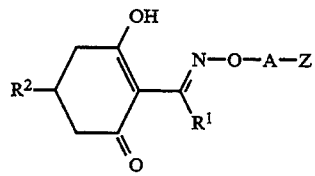

where, inter alia,
a) F is benzyl and E is 2-ethylthiopropyl (U.S. Pat. No. 4,440,566),
b) F is benzyl or but-2-enyl and E is a substituted 5-membered hetaryl radical (EP-A 238 021 and EP-A 125 094),
c) F is benzyl or 2-but-2-enyl and E is substituted phenyl (EP-A 80 301),
d) F is but-2-enyl and E is a 5-membered to 7-membered heterocyclic ring having not more than two O or S atoms and having not more than two double bonds (EPA 218 233) and
e) F is 4-phenylbutyl, 4-phenylbutyl-2-enyl or 4-phenyl-but-3-enyl and E is one of the radicals stated under a) to d) (prior German Application P 38 38 309), as herbicides.

It is an object of the present invention to provide compounds which, at a low application rate, have high selectivity, i.e. control undesirable plants without damaging the crops.

We have found that this object is achieved by the novel cyclohexenone oxime ethers of the formula I, which have a good herbicidal action against undesirable grasses. The compounds are tolerated by broad-leaved crops and some of them are tolerated by gramineous crops, such as rice.

The cyclohexenones of the formula I can be prepared in a conventional manner from known derivatives of the formula II (EP-A 80 301, EP-A 125 094, EP-A 142 741, U.S. Pat. No. 4 249 937, EP-A 137 174 and EP-A 177 913) and the corresponding hydroxylamines of the formula III (Houben-Weyl, 10/1, page 1181 et seq.) (EP-A 169 521).

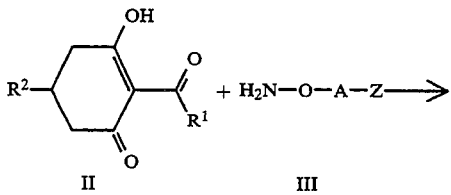

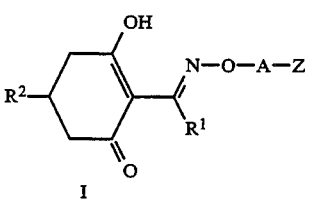

The reaction is advantageously carried out in the heterogeneous phase in a solvent at an adequate temperature below about 80° C., in the presence of a base, and the hydroxylamine III is used in the form of its ammonium salts.

Examples of suitable bases are carbonates, bicarbonates, acetates, alcoholates or oxides of alkali metals or alkaline earth metals, in particular sodium hydroxide, potassium hydroxide, magnesium oxide or calcium oxide. Furthermore, organic bases, such as pyridine or tertiary amines, can be used. The base is added, for example, in an amount of from 0.5 to 2 mol equivalents, based on the ammonium compound.

Examples of suitable solvents are dimethyl sulfoxide, alcohols, such as methanol, ethanol and isopropanol, aromatic hydrocarbons, such as benzene and toluene, chlorohydrocarbons, such as chloroform and dichloroethane, aliphatic hydrocarbons, such as hexane and cyclohexane, esters, such as ethyl acetate, and ethers, such as diethyl ether, dioxane and tetrahydrofuran. The reaction is preferably carried out in methanol using sodium bicarbonate as the base.

The reaction is complete after a few hours. The desired compound can be isolated, for example, by evaporating down the mixture, partitioning the residue between methylene chloride and water and distilling off the solvent under reduced pressure.

However, it is also possible to use the free hydroxylamine base directly, for example in the form of an aqueous solution, for this reaction; depending on the solvent used for the compound II, a one-phase or two-phase reaction mixture is obtained.

Examples of suitable solvents for this variant are alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

Alkali metal salts of the compounds I can be obtained by treating the 3-hydroxy compounds with sodium hydroxide, potassium hydroxide or a sodium or potassium alcoholate in aqueous solution or in an organic solvent, such as methanol, ethanol, acetone or toluene.

Other metal salts, such as manganese, copper, zinc, iron, calcium, magnesium and barium salts, can be prepared from the sodium salts in a conventional manner, as can ammonium and phosphonium salts using ammonia or phosphonium, sulfonium or sulfoxonium hydroxides.

The compounds of type II can be prepared, for example, from the corresponding cyclohexane-1,3-diones of the formula VII

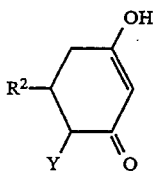

where Y is hydrogen or methoxycarbonyl, by known methods (Tetrahedron Lett.( 1975), 2491 ).

It is also possible to prepare the compounds of the formula II via the enol ester intermediates VIII, which are obtained in the reaction of compounds of the formula VII with acid chlorides IX in the presence of bases and are then subjected to a rearrangement reaction with certain imidazole or pyridine derivatives (Japanese Preliminary Published Application 79/063 052).

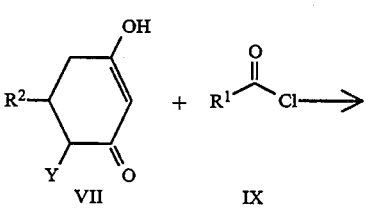

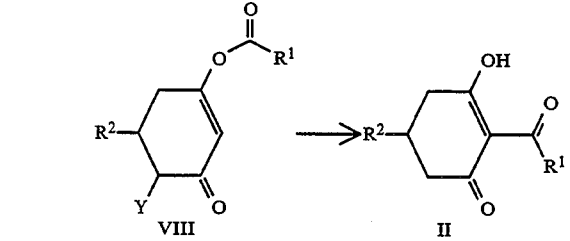

The compounds of the formula VII are obtained via a number of known process steps, starting from known intermediates.

The synthesis of the hydroxylamines III, in which A is a substituted or unsubstituted $C_3$-$C_6$-alkynylene bridge, is carried out according to the following reaction scheme, by methods known from the literature (J. Med. Chem. 29. (1986), 1389; EP-A 131 302; J. Med. Chem. 24 (1981), 678 and J. Chem. Ecol. 10 (1982), 1201), starting from aryl or hetaryl halides X, by coupling with a 1,ω-alkynol XIa in the presence of a palladium catalyst (cf. Tetrahedron Lett. 50 (1975), 4467). The alkynol IVa thus obtained is coupled with a cyclic hydroximide V.

Coupling may be effected directly by the Mitsunobu variant (Synthesis 1981, 1; J. Med. Chem. 33 (1990), 187) between the arylalkynol IVa and the cyclic hydroximide V, or by converting the OH group of the arylalkynol IVa into a leaving group X (e.g. halogen, O-mesylate, etc.) and then substituting the leaving group with the hydroximide V to give the imidoether VI.

Compounds in which the triple bond is not conjugated with the aromatic or heteroaromatic can be converted into the arylalkynol IVc, for example, by reacting an aralkyl halide XII with the dianion of a 1,ω-alkynol XI. The arylalkynol IVc can then be converted into the protected hydroxylamine derivative XIb, as described above, either directly or via the intermediate IVd.

The protected hydroxylamine derivative VI is cleaved with a base, for example with 2-aminoethanol, to give the free hydroxylamine III:

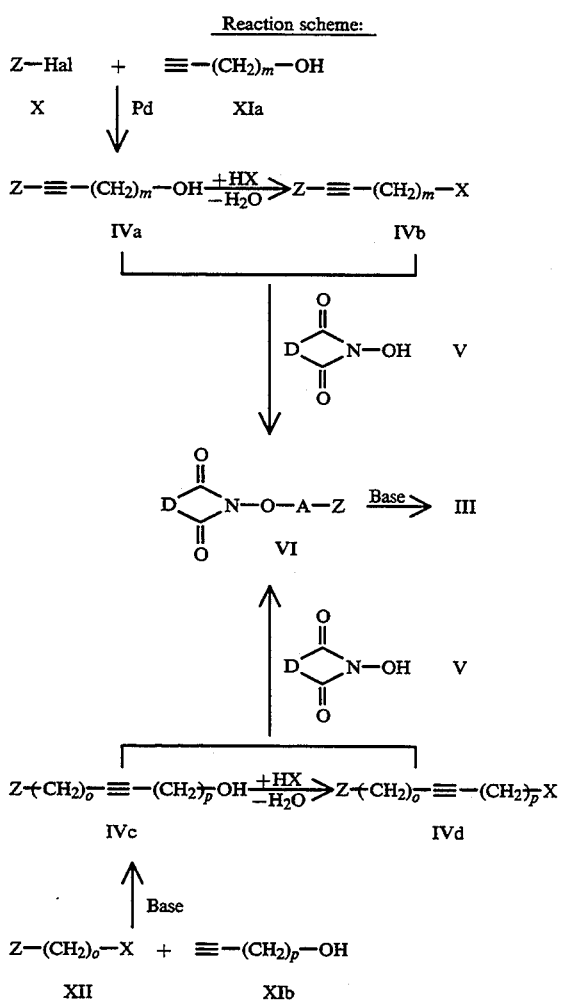

where Hal is Cl, Br or I, X is Cl, Br, mesylate or tosylate, m is 1, 2, 3 or 4, o and p are each 1, 2 or 3 and A is $C_3-C_6$-alkynylene.

In the cyclic hydroximides, D is, for example, phenylene, naphthylene, pyridinylene, cyclopentylene, cyclohexylene or cyclohexenylene. Examples of suitable substances are the following:

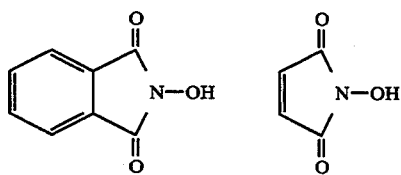

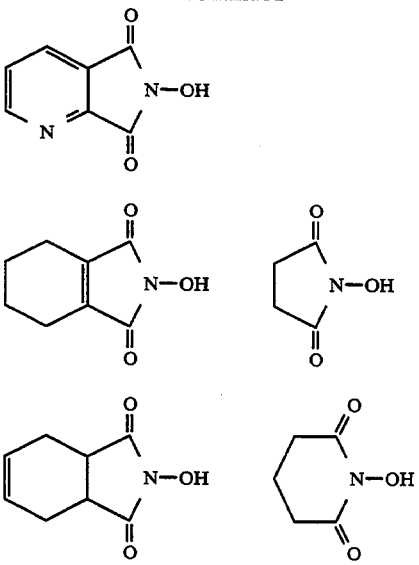

The reaction of the compounds IVb and IVd with the hydroximides V is advantageously carried out in the presence of a base. Suitable bases are in principle all those which are capable of deprotonating the hydroximides V without attacking the imide system. These are, in particular, the nonnucleophilic bases. Examples are mineral bases, such as alkali metal and alkaline earth metal carbonates, and alkali metal and alkaline earth metal bicarbonates, and organic bases, such as aliphatic, cycloaliphatic and aromatic tertiary a mines. Mixtures of these bases may also be used.

Examples of individual compounds are the following bases: sodium carbonate, potassium carbonate, magnesium carbonate, calcium carbonte, barium carbonate, the bicarbonates of these metals, trimethylamine, triethylamine, tributylamine, ethyldiisopropylamine, N,N-dimethylaniline, 4-N,N-dimethylaminopyridine, diazobicyclooctane, diazobicycloundecane, N-methylpiperidine, 1,4-dimethylpiperazine, pyridine, quinoline, bipyridine and phenanthroline. The economical bases sodium carbonate and potassium carbonate are preferred.

The base is added in general in an equivalent amount to an excess of 5 equivalents, based on the hydroximide. A larger excess is possible but has no additional advantages. It is also possible to use a smaller amount of base. However, the base is preferably used in an amount of from 1 to 3, in particular from 1 to 2, equivalents, based on the hydroximide V.

It is also possible to use nucleophilic bases, such as alkali metal hydroxides and alkaline earth metal hydroxides, in particular sodium hydroxide and potassium hydroxide. In this case, it is advantageous to use the base in an equivalent amount, based on the hydroximide VI, in order to avoid nucleophilic attack by the hydroxyl ions on the carbonyl function of the imide group.

Advantageously, the starting compounds VI are reacted with the hydroximides V in a solvent which is inert under the reaction conditions. Examples of advantageous solvents are polar aprotic solvents, such as dimethylformamide, N-methylpyrrolidone, dimethyl sulfoxide, sulfolane and cyclic ureas. The amount of solvent is generally not critical.

The reaction of the starting compounds IVb, d with the hydroximides V can also be carried out using phase transfer catalysis. In this case, solvents which form two phases with water, preferably chlorohydrocarbons, are used. Suitable phase transfer catalysts are the quaternary ammonium and phosphonium salts, polyethylene glycols, polyethylene glycol ethers and crown ethers usually used for such purposes, as described in, for example, Dehmlow et al., Phase Transfer Catalysis, pages 37–45 and pages 86–93, Verlag Chemie, Weinheim 1980. The phase transfer catalysts are advantageously used in amounts of from 1 to 10, preferably from 3 to 5,% by volume, based on the volume of the reaction mixture.

The reaction of the starting compounds IVb and IVd with the hydroximides V is carried out in general at from 0° to to 140° C., preferably from 20° to 100° C., in particular from 40° to 80° C. In an advantageous procedure, the hydroximide V is initially taken together with the base in the solvent, and the starting material VI is metered into this solution. It may prove advantageous to add the hydroximide at a lower temperature, for example at from 0° to 50° C., and not to heat the reaction mixture to the actual reaction temperature until after this addition.

After the end of the reaction, water is advantageously added to the cooled reaction mixture, the resulting hydroxylamine derivatives VI separating out as crystalline solids or as oils. The hydroxylamine derivatives obtained in this manner can, if desired, be further purified by recrystallization or by extraction.

In the reaction of the alkynols IVa or IVc with a cyclic hydroximide V by the Mitsunobu method, the cyclic imidoethers of the formula VI are likewise formed.

The coupling of the alcohols IVa, c to a hydroximide of the formula V is carried out in the presence of a triarylphosphine derivative and of an azodicarboxylic diester in an inert solvent (J. Med. Chem. 33 (1990), 187). For reasons, of cost, a preferably used hydroximide V is hydroxyphthalimide.

The phosphine derivative used is, for example, triphenylphosphine, and the diethyl ester is preferably used as the azodicarboxylic diester.

Suitable solvents are aprotic organic solvents, for example diethyl ether, tetrahydrofuran, toluene and ethyl acetate.

The hydroxylamine derivatives VI can be temporarily stored or immediately converted into the hydroxylamine derivatives III having a free amino group. This conversion can be carried out by conventional processes, as described, for example, in DE-A 36 15 973 and in the publications cited therein. A preferably used process is that according to DE-A 36 15 973, in which the hydroxylamine derivatives III are liberated by means of ethanolamine. Liberation of the hydroxylamine derivatives III with the aid of other bases, such as aqueous mineral bases, or with amines, hydrazines, hydroxylamines or aqueous acids is also possible.

The hydroxylamine derivatives III can be isolated from the reaction mixtures obtained by these processes by conventional methods of working up, for example by extraction or by crystallization. To increase the tendency of these hydroxylamine derivatives to crystallize, it may often be necessary to convert them into their salts with mineral acids or organic acids. For this purpose, in general dilute solutions of these acids are reacted with the hydroxylamine derivatives, advantageously in equivalent amounts. The resulting hydroxylammonium salts can, as in the case of the hydroxylamine derivatives having a free amino group, be further processed directly to give the herbicides of the formula I or, if desired, stored.

Because of the biological activity, preferred cyclohexenones of the formula I are those in which the substituents have the following meanings:

$R^1$ is alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular ethyl or propyl;

A is alkynylene, such as prop-2-ynylene, but-2-ynylene, but-3-ynylene, pent-2-ynylene, pent-4-ynylene, hex-2-ynylene, hex-3-ynylene, hex-4-ynylene, hex-5-ynylene, pent-2-yn-4-enylene, pent-4-yn-2-enylene, hex-2-yn-4-enylene, hex-2-yn-5-enylene, hex-3-yn-5-enylene, hex-4-yn-2-enylene, hex-5-yn-2-enylene or hex-5-yn-3-enylene, and may be substituted by 1 to 3 methyl or ethyl radicals and/or fluorine or chlorine; in the case of the unsaturated chains, both the cis and the trans form may occur; but-2-ynylene, but-3-ynylene and prop-2-ynylene are particularly preferred;

Z is phenyl, thiophene, furan, pyrrole, thiazole, oxazole, imidazole, isothiazole, isoxazole, pyrazole, pyridine, pyrimidine, pyrazine, pyridazine or triazine; phenyl, thiophene, furan, thiazole, pyridine and pyrimidine are preferred, and phenyl, thiophene and pyridine are particularly preferred;

X is halogen, such as fluorine, chlorine, bromine or iodine, in particular fluorine or chlorine; alkyl, such as methyl, ethyl, propyl, 1-methylethyl, butyl, 1-methylpropyl, 2-methylpropyl or 1,1-dimethylethyl, in particular methyl or 1,1-dimethylethyl, alkoxy, such as methoxy, ethoxy, propoxy, 1-methylethoxy, butoxy, 1-methylpropoxy, 2-methylpropoxy or 1,1-dimethylethoxy, in particular methoxy, ethoxy, 1-methylethoxy or 1,1-dimethylethoxy, alkylthio, such as methylthio, ethylthio, propylthio, 1-methylethylthio, butylthio, 1-methylpropylthio, 2-methylpropylthio or 1,1-dimethylethylthio, in particular methylthio or ethylthio, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular difluoromethyl, trifluoromethyl, 2,2,2-trifluoroethyl or pentafluoroethyl, haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy, alkoxycarbonyl, such as methoxycarbonyl, ethoxycarbonyl, propoxycarbonyl, 1-methylethoxycarbonyl, butoxycarbonyl or 1,1-dimethylethoxycarbonyl, in particular methoxycarbonyl, ethoxycarbonyl or 1,1-dimethylethoxycarbonyl, in particular methoxycarbonyl, nitro, cyano or benzyloxycarbonyl or phenyl, where the aromatic radicals in turn may carry one to three of the following radicals: nitro, cyano, carboxyl, benzyloxycarbonyl, halogen as stated in general and in particular for X, alkyl as stated for $R^1$, in particular methyl, ethyl or 1-methylethyl, alkoxy as stated above in particular methoxy or ethoxy, alkylthio as stated above, in particular methylthio, haloalkyl as stated above, in particular trifluoromethyl, haloalkoxy as stated above, in particular difluoromethoxy or trifluoromethoxy, and/or alkoxycarbonyl as stated above, in particular methoxycarbonyl or ethoxycarbonyl.

Particularly preferred among these aromatic radicals are those which are unsubstituted or monosubstituted.

n is 0, 1, 2 or 3, particularly 0, 1 or 2. In the case of a plurality of radicals X, the substituents may be identical or different.

$R^2$ is alkyl as stated under $R^1$, which may carry one of the alkoxy or alkylthio groups stated under X, preferably in the 1-, 2- or 3-position, in particular 2-ethylthiopropyl, 5-membered heterocycloalkyl, such as tetrahydrofuranyl, tetrahydrothienyl, dioxolanyl, dithiolanyl or oxathiolanyl, in particular tetrahydrofuranyl, tetrahydrothienyl or dioxolanyl, where these rings may carry one to three of the $C_1$–$C_4$-alkyl groups, $C_1$–$C_4$-alkoxy groups, $C_1$–$C_4$-alkylthio groups and/or $C_1$–$C_4$-haloalkyl groups stated above under X, 5-membered hetaryl, such as pyrrolyl, pyrazolyl, imidazolyl, isoxazolyl, oxazolyl, isothiazolyl, thiazolyl, furanyl or thienyl, in particular isoxazolyl or furanyl, a 6-membered or 7-membered heterocyclic structure, such as tetrahydropyran-3-yl, dihydropyran-3-yl, tetrahydropyran-4-yl, dihydropyran-4-yl, tetrahydrothiopyran-3-yl, dihydrothiopyran-3-yl, tetrahydrothiopyran-4-yl, dihydrothiopyran-4-yl or dioxepan-5-yl, in particular tetrahydropyran-3-yl, tetrahydropyran-4-yl or tetrahydrothiopyran-3-yl, phenyl or pyridyl, where the cyclic radicals may carry one to three of the alkyl groups, alkoxy groups, alkylthio groups and/or haloalkyl groups stated under X.

The 5-membered heteroaromatics $R^2$ may carry the following radicals as substituents:

halogen as stated under X, in particular fluorine or chlorine, alkoxyalkyl, such as methoxymethyl, 2-methoxyethyl, 2-methoxypropyl, 3-methoxypropyl, 2-methoxy-1-methylethyl, ethoxymethyl, 2-ethoxyethyl, 2-ethoxypropyl, 3-ethoxypropyl, 3-ethoxypropyl, 2-ethoxy-1-methylethyl or 1-ethoxy-1-methylethyl, in particular methoxyethyl or ethoxyethyl, alkenyl, such as ethenyl, 1-propenyl, 2-propenyl, 1methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, in particular 1-methylethenyl or corresponding alkenyloxy and/or haloalkenyl radicals.

The 6-membered and 7-membered heterocylic structures may also carry hydroxyl groups in addition to the abovementioned substituents.

In the case of the phenyl and pyridyl radicals, suitable substituents in addition to the abovementioned groups are the following radicals:

alkenyloxy, such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 1-ethyl-2-butenyloxy, 1-enhyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy or 1-ethyl-2-methyl-2-propenyloxy, in particular 2-propenyloxy or 2-butenyloxy;

alkynyloxy, such as 2-propynyloxy, 2-butynyloxy, 3-butynyloxy, 1-methyl-2-propynyloxy, 2-pentynyloxy, 3-pentynyloxy, 4-pentynyloxy, 1-methyl-3-butynyloxy, 2-methyl-3-butynyloxy, 1-methyl-2-butynyloxy, 1,1-dimethyl-2-propynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy or 1-ethyl-1-methyl-2-propynyloxy, in particular 2-propynyloxy or 2-butynyloxy;

$C_1$–$C_4$alkyl, as stated in general and in particular above for X, which is substituted by $C_1$–$C_4$alkoxy, as stated above in general and in particular for X, preferably methoxymethyl, ethoxymethyl, 1-methoxyethyl, 2-methoxyethyl, 1-ethoxyethyl or 2-ethoxyethyl;

amino which may carry one or two of the following radicals: alkyl as stated for X, in particular methyl or ethyl; alkenyl as stated above, in particular 2-propenyl or 2-butenyl; alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-3-butynyl, 2-methyl-3-butynyl, 1-methyl-2-butynyl, 3-methyl-1-butynyl, 1,1-dimethyl-2-propynyl, 1-ethyl-2-propynyl, 1-hexynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl, in particular 2-propynyl or 2-butynyl and/or acyl, such as acetyl, propionyl, butyryl, 2-methylpropionyl, pentanoyl, 2-methylbutyryl, 3-methylbutyryl, 2,2-dimethylpropionyl, hexanoyl, 2-methylpentanoyl, 3-methylpentanoyl, 4-methylpentanoyl, 2,2-dimethylbutyryl, 2,3-dimethylbutyryl, 3,3-dimethylbutyryl or 2-ethylbutyryl, in particular acetyl or propionyl, or benzoyl.

Particularly preferred cyclohexenone oxime ethers of the formula I are summarized in the Tables below.

TABLE A

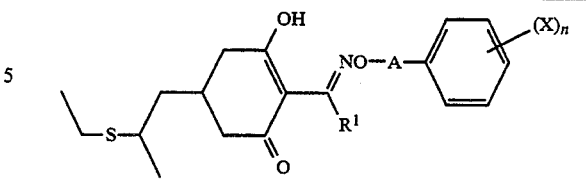

| $R^1$ | A | X | n |
|---|---|---|---|
| $CH_2CH_3$ | $CH_2-C{\equiv}C$ | — | 0 |
| $(CH_2)_2CH_3$ | $CH_2-CH_2-C{\equiv}C$ | — | 0 |

TABLE A-continued

| $R^1$ | A | X | n |
|---|---|---|---|
| $CH_2CH_3$ | $CH_2-C{\equiv}C-CH_2$ | — | 0 |
| $(CH_2)_2CH_3$ | $CH_2-CH_2-CH_2-C{\equiv}C$ | — | 0 |
| $CH_2CH_3$ | $CH_2-CH_2-C{\equiv}C-CH_2$ | 4-$CF_3$ | 1 |
| $(CH_2)_2CH_3$ | $CH_2-C{\equiv}C-CH_2-CH_2$ | 4-$CF_3$ | 1 |
| $CH_2CH_3$ | $CH_2-CH_2-CH_2-C{\equiv}C-CH_2$ | 3-F | 1 |
| $(CH_2)_2CH_3$ | $CH_2-CH_2-C{\equiv}C-CH_2-CH_2$ | 3-F | 1 |
| $CH_2CH_3$ | $CH_2-C{\equiv}C-CH_2-CH_2-CH_2$ | 4-F | 1 |
| $(CH_2)_2CH_3$ | $CH_2-C{\equiv}C$ | 4-F | 1 |
| $CH_2CH_3$ | $CH_2-CH_2-C{\equiv}C$ | 3-$CH_3$ | 1 |
| $(CH_2)_2CH_3$ | $CH_2-C{\equiv}C-CH_2$ | 3-$CH_3$ | 1 |
| $CH_2CH_3$ | $CH_2-CH_2-CH_2-C{\equiv}C$ | 4-$OCH_3$ | 1 |
| $(CH_2)_2CH_3$ | $CH_2-CH_2-C{\equiv}C-CH_2$ | 4-$OCH_3$ | 1 |
| $CH_2CH_3$ | $CH_2-C{\equiv}C-CH_2-CH_2$ | 3-$NO_2$ | 1 |
| $(CH_2)_2CH_3$ | $CH_2-CH_2-CH_2-C{\equiv}C-CH_2$ | 3-$NO_2$ | 1 |
| $CH_2CH_3$ | $CH_2-CH_2-C{\equiv}C-CH_2-CH_2$ | 3-CN | 1 |
| $(CH_2)_2CH_3$ | $CH_2-C{\equiv}C-CH_2-CH_2-CH_2$ | 3-CN | 1 |
| $CH_2CH_3$ | $CH_2-C{\equiv}C$ | 3-$CO_2CH_3$ | 1 |
| $(CH_2)_2CH_3$ | $CH_2-CH_2-C{\equiv}C$ | 3-$CO_2CH_3$ | 1 |
| $CH_2CH_3$ | $CH_2-C{\equiv}C-CH_2$ | 3-$CO_2Ph$ | 1 |
| $(CH_2)_2CH_3$ | $CH_2-CH_2-CH_2-C{\equiv}C$ | 3-$CO_2Ph$ | 1 |
| $CH_2CH_3$ | $CH_2-CH_2-C{\equiv}C-CH_2$ | 4-$OCHF_2$ | 1 |
| $(CH_2)_2CH_3$ | $CH_2-C{\equiv}C-CH_2-CH_2$ | 4-$OCHF_2$ | 1 |
| $CH_2CH_3$ | $CH_2-CH_2-CH_2-C{\equiv}C-CH_2$ | 3-$CH_3$, 4-Cl | 2 |
| $(CH_2)_2CH_3$ | $CH_2-CH_2-C{\equiv}C-CH_2-CH_2$ | 3-$CH_3$, 4-Cl | 2 |

TABLE B

| $R^1$ | $R^2$ | A | X | n |
|---|---|---|---|---|
| $CH_2CH_3$ | tetrahydrofuranyl | $CH_2-C{\equiv}C$ | — | 0 |
| $(CH_2)_2CH_3$ | tetrahydrofuranyl | $CH_2-C{\equiv}C-CH_2$ | — | 0 |
| $CH_2CH_3$ | tetrahydrofuranyl | $CH_2-CH_2-C{\equiv}C$ | 4-F | 1 |
| $(CH_2)_2CH_3$ | tetrahydrofuranyl | $CH_2-CH_2-CH_2-C{\equiv}C$ | 4-F | 1 |
| $CH_2CH_3$ | tetrahydrofuranyl | $CH_2-CH_2-C{\equiv}C-CH_2$ | 3-$CH_3$ | 1 |
| $(CH_2)_2CH_3$ | tetrahydrofuranyl | $CH-C{\equiv}C-CH_2-CH_2$ | 3-$CH_3$ | 1 |

TABLE B-continued $$\text{(structure: cyclohexenone with OH, =NOA-Ar(X)}_n\text{, R}^1\text{, R}^2\text{)}$$

| $R^1$ | $R^2$ | A | X | n |
|---|---|---|---|---|
| $CH_2CH_3$ | 3-tetrahydrofuranyl | $CH_2-CH_2-CH_2-CH_2-C\equiv C$ | 3-$CF_3$ | 1 |
| $(CH_2)_2CH_3$ | 3-tetrahydrofuranyl | $CH_2-CH_2-CH_2-C\equiv C-CH_2$ | 3-$CF_3$ | 1 |
| $CH_2CH_3$ | 3-tetrahydrofuranyl | $CH_2-CH_2-C\equiv C-CH_2-CH_2$ | 4-$C(CH_3)_3$ | 1 |
| $(CH_2)_2CH_3$ | 3-tetrahydrofuranyl | $CH_2-C\equiv C-CH_2-CH_2-CH_2$ | 4-$C(CH_3)_3$ | 1 |
| $CH_2CH_3$ | 3-tetrahydrofuranyl | $CH_2-C\equiv C$ | 3-Cl | 1 |
| $(CH_2)_2CH_3$ | 3-tetrahydrofuranyl | $CH_2-CH_2-C\equiv C$ | 3-Cl | 1 |
| $CH_2CH_3$ | 1,3-dioxolan-2-yl | $CH_2-CH_2-CH_2-CH_2-C\equiv C$ | 4-F | 1 |
| $(CH_2)_2CH_3$ | 1,3-dioxolan-2-yl | $CH_2-CH_2-CH_2-C\equiv C-CH_2$ | 4-F | 1 |
| $CH_2CH_3$ | 1,3-dioxolan-2-yl | $CH_2-CH_2-C\equiv C-CH_2-CH_2$ | 3-$CH_3$ | 1 |
| $(CH_2)_2CH_3$ | 1,3-dioxolan-2-yl | $CH_2-C\equiv C-CH_2-CH_2-CH_2$ | 3-$CH_3$ | 1 |
| $CH_2CH_3$ | 1,3-dioxolan-2-yl | $CH_2-C\equiv C$ | 3-$CF_3$ | 1 |
| $(CH_2)_2CH_3$ | 1,3-dioxolan-2-yl | $CH_2-CH_2-C\equiv C$ | 3-$CF_3$ | 1 |
| $CH_2CH_3$ | 1,3-dioxolan-2-yl | $CH_2-C\equiv C-CH_2$ | 4-$C(CH_3)_3$ | 1 |
| $(CH_2)_2CH_3$ | 1,3-dioxolan-2-yl | $CH_2-CH_2-CH_2-C\equiv C$ | 4-$C(CH_3)_3$ | 1 |

TABLE B-continued $$\text{structure: cyclohexanone with OH, R}^2\text{, and C(R}^1\text{)=N-O-A-C}_6\text{H}_{4}(X)_n$$

| R¹ | R² | A | X | n |
|---|---|---|---|---|
| CH₂CH₃ | 2-(1,3-dioxolanyl) | CH₂—CH₂—C≡C—CH₂ | 3-Cl | 1 |
| (CH₂)₂CH₃ | 2-(1,3-dioxolanyl) | CH₂—C≡C—CH₂—CH₂ | 3-Cl | 1 |
| CH₂CH₃ | 2-(4,5-dimethyl-1,3-dioxolanyl) | CH₂—CH₂—CH₂—CH₂—C≡C | — | 0 |
| (CH₂)₂CH₃ | 2-(4,5-dimethyl-1,3-dioxolanyl) | CH₂—CH₂—CH₂—C≡C—CH₂ | — | 0 |
| CH₂CH₃ | 2-(4,5-dimethyl-1,3-dioxolanyl) | CH₂—CH₂—C≡C—CH₂—CH₂ | 4-F | 1 |
| CH₂CH₃ | tetrahydrothiophen-3-yl | CH₂—C≡C—CH₂ | — | 0 |
| (CH₂)₂CH₃ | tetrahydrothiophen-3-yl | CH₂—CH₂—CH₂—C≡C | — | 0 |
| CH₂CH₃ | tetrahydrothiophen-3-yl | CH₂—CH₂—C≡C—CH₂ | 4-F | 1 |
| (CH₂)₂CH₃ | tetrahydrothiophen-3-yl | CH₂—C≡C—CH₂—CH₂ | 4-F | 1 |
| CH₂CH₃ | tetrahydrothiophen-3-yl | CH₂—CH₂—CH₂—CH₂—C≡C | 3-CH₃ | 1 |
| (CH₂)₂CH₃ | tetrahydrothiophen-3-yl | CH₂—CH₂—CH₂—C≡C—CH₂ | 3-CH₃ | 1 |
| CH₂CH₃ | tetrahydrothiophen-3-yl | CH₂—CH₂—C≡C—CH₂—CH₂ | 3-CF₃ | 1 |
| (CH₂)₂CH₃ | tetrahydrothiophen-3-yl | CH₂—C≡C—CH₂—CH₂—CH₂ | 3-CF₃ | 1 |
| CH₂CH₃ | tetrahydrothiophen-3-yl | CH₂—C≡C | 4-C(CH₃)₃ | 1 |

TABLE B-continued

| R¹ | R² | A | X | n |
|---|---|---|---|---|
| (CH₂)₂CH₃ | 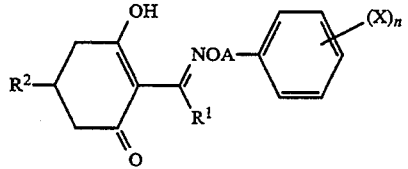 tetrahydrothiophene-3-yl | CH₂—CH₂—C≡C | 4-C(CH₃)₃ | 1 |
| CH₂CH₃ | 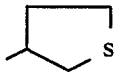 tetrahydrothiophene-3-yl | CH₂—C≡C—CH₂ | 3-Cl | 1 |
| (CH₂)₂CH₃ |  tetrahydrothiophene-3-yl | CH₂—CH₂—CH₂—C≡C | 3-Cl | 1 |
| CH₂CH₃ |  1,3-dioxolan-2-yl | CH₂—CH₂—C≡C—CH₂ | — | 0 |
| (CH₂)₂CH₃ | 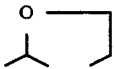 1,3-dioxolan-2-yl | CH₂—C≡C—CH₂—CH₂ | — | 0 |
| (CH₂)₂CH₃ | 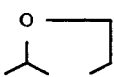 4,5-dimethyl-1,3-dioxolan-2-yl | CH₂—C≡C—CH₂—CH₂—CH₂ | 4-F | 1 |
| CH₂CH₃ | 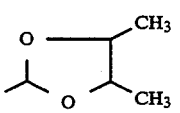 4,5-dimethyl-1,3-dioxolan-2-yl | CH₂—C≡C | 3-CH₃ | 1 |
| (CH₂)₂CH₃ | 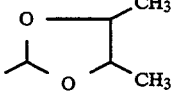 4,5-dimethyl-1,3-dioxolan-2-yl | CH₂—CH₂—C≡C | 3-CH₃ | 1 |
| CH₂CH₃ | 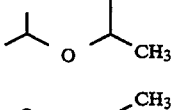 4,5-dimethyl-1,3-dioxolan-2-yl | CH₂—C≡C—CH₂ | 3-CF₃ | 1 |
| (CH₂)₂CH₃ | 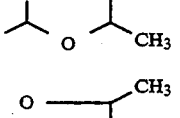 4,5-dimethyl-1,3-dioxolan-2-yl | CH₂—CH₂—CH₂—C≡C | 3-CF₃ | 1 |
| CH₂CH₃ | 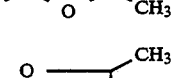 4,5-dimethyl-1,3-dioxolan-2-yl | CH₂—CH₂—C≡C—CH₂ | 4-C(CH₃)₃ | 1 |
| (CH₂)₂CH₃ | 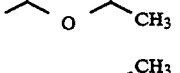 4,5-dimethyl-1,3-dioxolan-2-yl | CH₂—C≡C—CH₂—CH₂ | 4-C(CH₃)₃ | 1 |
| CH₂CH₃ | 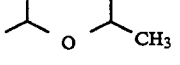 4,5-dimethyl-1,3-dioxolan-2-yl | CH₂—CH₂—CH₂—CH₂—C≡C | 3-Cl | 1 |

TABLE B-continued

Structure: cyclohexenone with OH, R² substituent, =N-O-A-C₆H₄(X)ₙ oxime ether, and R¹ on the imine carbon.

| R¹ | R² | A | X | n |
|---|---|---|---|---|
| (CH₂)₂CH₃ | 2,2-(4,5-dimethyl-1,3-dioxolane) | CH₂—CH₂—CH₂—C≡C—CH₂ | 3-Cl | 1 |
| CH₂CH₃ | 2-isopropyl-1,3-dithiolane | CH₂—CH₂—C≡C—CH₂—CH₂ | — | 0 |
| (CH₂)₂CH₃ | 2-isopropyl-1,3-dithiolane | CH₂—C≡C—CH₂—CH₂—CH₂ | — | 0 |
| CH₂CH₃ | 2-isopropyl-1,3-dithiolane | CH₂—C≡C | 4-F | 1 |
| (CH₂)₂CH₃ | 2-isopropyl-1,3-dithiolane | CH₂—CH₂—C≡C | 4-F | 1 |
| CH₂CH₃ | 2-isopropyl-1,3-dithiolane | CH₂—C≡C—CH₂ | 3-CH₃ | 1 |
| (CH₂)₂CH₃ | 2-isopropyl-1,3-dithiolane | CH₂—CH₂—CH₂—C≡C | 3-CH₃ | 1 |
| CH₂CH₃ | 2-isopropyl-1,3-dithiolane | CH₂—CH₂—C≡C—CH₂ | 3-CF₃ | 1 |
| (CH₂)₂CH₃ | 2-isopropyl-1,3-dithiolane | CH₂—C≡C—CH₂—CH₂ | 3-CF₃ | 1 |
| CH₂CH₃ | 2-isopropyl-1,3-dithiolane | CH₂—CH₂—CH₂—CH₂—C≡C | 4-C(CH₃)₃ | 1 |
| (CH₂)₂CH₃ | 2-isopropyl-1,3-dithiolane | CH₂—CH₂—CH₂—C≡C—CH₂ | 4-C(CH₃)₃ | 1 |
| CH₂CH₃ | 2-isopropyl-1,3-dithiolane | CH₂—CH₂—C≡C—CH₂—CH₂ | 3-Cl | 1 |
| (CH₂)₂CH₃ | 2-isopropyl-1,3-dithiolane | CH₂—C≡C—CH₂—CH₂—CH₂ | 3-Cl | 1 |

TABLE B-continued

Structure: cyclohexanone with OH, R², and =N-OA-C₆H₄-(X)ₙ oxime ether group, R¹ on the imine carbon.

| R¹ | R² | A | X | n |
|---|---|---|---|---|
| CH₂CH₃ | 4-(tetrahydropyranyl-3-ene) | CH₂—C≡C | — | 0 |
| (CH₂)₂CH₃ | 4-(tetrahydropyranyl-3-ene) | CH₂—CH₂—C≡C | — | 0 |
| CH₂CH₃ | 4-(tetrahydropyranyl-3-ene) | CH₂—C≡C—CH₂ | 4-F | 1 |
| (CH₂)₂CH₃ | 4-(tetrahydropyranyl-3-ene) | CH₂—CH₂—CH₂—C≡C | 4-F | 1 |
| CH₂CH₃ | 4-(tetrahydropyranyl-3-ene) | CH₂—CH₂—C≡C—CH₂ | 3-CH₃ | 1 |
| (CH₂)₂CH₃ | 4-(tetrahydropyranyl-3-ene) | CH₂—C≡C—CH₂—CH₂ | 3-CH₃ | 1 |
| CH₂CH₃ | 4-(tetrahydropyranyl-3-ene) | CH₂—CH₂—CH₂—CH₂—C≡C | 3-CF₃ | 1 |
| (CH₂)₂CH₃ | 4-(tetrahydropyranyl-3-ene) | CH₂—CH₂—CH₂—C≡C—CH₂ | 3-CF₃ | 1 |
| CH₂CH₃ | 4-(tetrahydropyranyl-3-ene) | CH₂—CH₂—C≡C—CH₂—CH₂ | 4-C(CH₃)₃ | 1 |
| (CH₂)₂CH₃ | 4-(tetrahydropyranyl-3-ene) | CH₂—C≡C—CH₂—CH₂—CH₂ | 4-C(CH₃)₃ | 1 |
| CH₂CH₃ | 4-(tetrahydropyranyl-3-ene) | CH₂—C≡C | 3-Cl | 1 |

TABLE B-continued

| R¹ | R² | A | X | n |
|---|---|---|---|---|
| (CH₂)₂CH₃ | (tetrahydropyranylidene-methyl) | CH₂—CH₂—C≡C | 3-Cl | 1 |
| CH₂CH₃ | 3,3-dibromo-tetrahydropyran-4-yl | CH₂—C≡C—CH₂ | — | 0 |
| (CH₂)₂CH₃ | 3,3-dibromo-tetrahydropyran-4-yl | CH₂—CH₂—CH₂—C≡C | — | 0 |
| CH₂CH₃ | 3,3-dibromo-tetrahydropyran-4-yl | CH₂—CH₂—C≡C—CH₂ | 4-F | 1 |
| (CH₂)₂CH₃ | 3,3-dibromo-tetrahydropyran-4-yl | CH₂—C≡C—CH₂—CH₂ | 4-F | 1 |
| CH₂CH₃ | 3,3-dibromo-tetrahydropyran-4-yl | CH₂—CH₂—CH₂—CH₂—C≡C | 3-CH₃ | 1 |
| (CH₂)₂CH₃ | 3,3-dibromo-tetrahydropyran-4-yl | CH₂—CH₂—CH₂—C≡C—CH₂ | 3-CH₃ | 1 |
| CH₂CH₃ | 3,3-dibromo-tetrahydropyran-4-yl | CH₂—CH₂—C≡C—CH₂—CH₂ | 3-CF₃ | 1 |
| (CH₂)₂CH₃ | 3,3-dibromo-tetrahydropyran-4-yl | CH₂—C≡C—CH₂—CH₂—CH₂ | 3-CF₃ | 1 |

TABLE B-continued

Structure: Cyclohexane ring with OH, R², =N-O-A-phenyl-(X)ₙ, R¹, and =O substituents as shown.

| R¹ | R² | A | X | n |
|---|---|---|---|---|
| CH₂CH₃ | 3,4-dibromo-3-methyltetrahydropyran | CH₂—C≡C | 4-C(CH₃)₃ | 1 |
| (CH₂)₂CH₃ | 3,4-dibromo-3-methyltetrahydropyran | CH₂—CH₂—C≡C | 4-C(CH₃)₃ | 1 |
| CH₂CH₃ | 3,4-dibromo-3-methyltetrahydropyran | CH₂—C≡C—CH₂ | 3-Cl | 1 |
| (CH₂)₂CH₃ | 3,4-dibromo-3-methyltetrahydropyran | CH₂—CH₂—CH₂—C≡C | 3-Cl | 1 |
| CH₂CH₃ | 3-methylisothiazol-5-yl | CH₂—CH₂—C≡C—CH₂ | — | 0 |
| (CH₂)₂CH₃ | 3-methylisothiazol-5-yl | CH₂—C≡C—CH₂—CH₂ | — | 0 |
| CH₂CH₃ | 3-methylisothiazol-5-yl | CH₂—CH₂—CH₂—CH₂—C≡C | 4-F | 1 |
| (CH₂)₂CH₃ | 3-methylisothiazol-5-yl | CH₂—CH₂—CH₂—C≡C—CH₂ | 4-F | 1 |
| CH₂CH₃ | 3-methylisothiazol-5-yl | CH₂—CH₂—C≡C—CH₂—CH₂ | 3-CH₃ | 1 |
| (CH₂)₂CH₃ | 3-methylisothiazol-5-yl | CH₂—C≡C—CH₂—CH₂—CH₂ | 3-CH₃ | 1 |
| CH₂CH₃ | 3-methylisothiazol-5-yl | CH₂—C≡C | 3-CF₃ | 1 |
| (CH₂)₂CH₃ | 3-methylisothiazol-5-yl | CH₂—CH₂—C≡C | 3-CF₃ | 1 |

TABLE B-continued

| R¹ | R² | A | X | n |
|---|---|---|---|---|
| $CH_2CH_3$ | isothiazol-5-yl | $CH_2-C\equiv C-CH_2$ | $4-C(CH_3)_3$ | 1 |
| $(CH_2)_2CH_3$ | isothiazol-5-yl | $CH_2-CH_2-CH_2-C\equiv C$ | $4-C(CH_3)_3$ | 1 |
| $CH_2CH_3$ | isothiazol-5-yl | $CH_2-CH_2-C\equiv C-CH_2$ | 3-Cl | 1 |
| $(CH_2)_2CH_3$ | isothiazol-5-yl | $CH_2-C\equiv C-CH_2-CH_2$ | 3-Cl | 1 |
| $CH_2CH_3$ | 2,2-dimethyl-1,3-dioxan-5-yl | $CH_2-CH_2-CH_2-CH_2-C\equiv C$ | $3-CF_3$ | 1 |
| $(CH_2)_2CH_3$ | 2,2-dimethyl-1,3-dioxan-5-yl | $CH_2-CH_2-CH_2-C\equiv C-CH_2$ | $3-CF_3$ | 1 |
| $CH_2CH_3$ | 2,2-dimethyl-1,3-dioxan-5-yl | $CH_2-CH_2-C\equiv C-CH_2-CH_2$ | $4-C(CH_3)_3$ | 1 |
| $(CH_2)_2CH_3$ | 2,2-dimethyl-1,3-dioxan-5-yl | $CH_2-C\equiv C-CH_2-CH_2-CH_2$ | $4-C(CH_3)_3$ | 1 |
| $CH_2CH_3$ | 2,2-dimethyl-1,3-dioxan-5-yl | $CH_2-C\equiv C$ | — | 0 |
| $(CH_2)_2CH_3$ | 2,2-dimethyl-1,3-dioxan-5-yl | $CH_2-CH_2-C\equiv C$ | — | 0 |
| $CH_2CH_3$ | 1,3-dioxolan-4-yl | $CH_2-C\equiv C-CH_2$ | — | 0 |
| $(CH_2)_2CH_3$ | 1,3-dioxolan-4-yl | $CH_2-C\equiv C-CH_2$ | — | 0 |
| $CH_2CH_3$ | 1,3-dioxolan-4-yl | $CH_2-CH_2-CH_2-C\equiv C$ | $3-CF_3$ | 1 |

TABLE B-continued
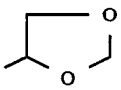
| R¹ | R² | A | X | n |
|---|---|---|---|---|
| (CH₂)₂CH₃ | 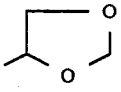 | CH₂—CH₂—C≡C—CH₂ | 3-CF₃ | 1 |
| CH₂CH₃ | 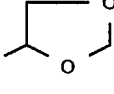 | CH₂—C≡C—CH₂—CH₂ | 4-C(CH₃)₃ | 1 |
| (CH₂)₂CH₃ | 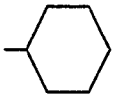 | CH₂—CH₂—CH₂—CH₂—C≡C | 4-C(CH₃)₃ | 1 |
| CH₂CH₃ | 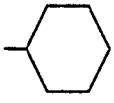 | CH₂—CH₂—CH₂—C≡C—CH₂ | — | 0 |
| (CH₂)₂CH₃ | 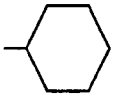 | CH₂—CH₂—C≡C—CH₂—CH₂ | — | 0 |
| CH₂CH₃ |  | CH₂—C≡C—CH₂—CH₂—CH₂ | 3-CF₃ | 1 |
| (CH₂)₂CH₃ | 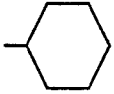 | CH₂—C≡C | 3-CF₃ | 1 |
| CH₂CH₃ | 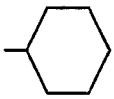 | CH₂—CH₂—C≡C | 4-C(CH₃)₃ | 1 |
| (CH₂)₂CH₃ | 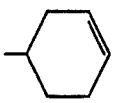 | CH₂—C≡C—CH₂ | 4-C(CH₃)₃ | 1 |
| CH₂CH₃ | 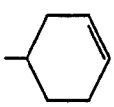 | CH₂—CH₂—CH₂—C≡C | — | 0 |
| (CH₂)₂CH₃ | 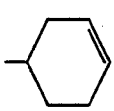 | CH₂—CH₂—C≡C | — | 0 |
| CH₂CH₃ | 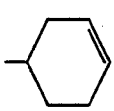 | CH₂—C≡C—CH₂ | 3-CF₃ | 1 |

TABLE B-continued
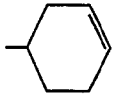
| R¹ | R² | A | X | n |
|---|---|---|---|---|
| $(CH_2)_2CH_3$ | 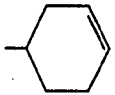 | $CH_2-C\equiv C$ | 3-$CF_3$ | 1 |
| $CH_2CH_3$ | 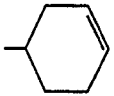 | $CH_2-C\equiv C-CH_2$ | 4-$C(CH_3)_3$ | 1 |
| $(CH_2)_2CH_3$ | 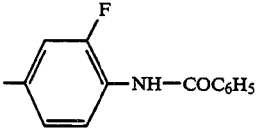 | $CH_2-CH_2-C\equiv C$ | 4-$C(CH_3)_3$ | 1 |
| $(CH_2)_2CH_3$ | 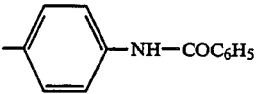 | $CH_2-C\equiv C-CH_2$ | — | 0 |
| $CH_2CH_3$ | 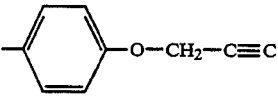 | $CH_2-CH_2-CH_2-C\equiv C$ | 3-$CF_3$ | 1 |
| $(CH_2)_2CH_3$ | 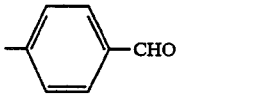 | $CH_2-CH_2-C\equiv C-CH_2$ | 3-$CF_3$ | 1 |
| $CH_2CH_3$ | 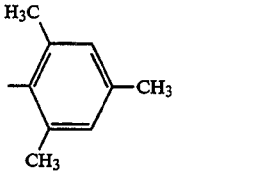 | $CH_2-C\equiv C-CH_2-CH_2$ | 4-$C(CH_3)_3$ | 1 |
| $(CH_2)_2CH_3$ | 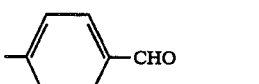 | $CH_2-CH_2-CH_2-CH_2-C\equiv C$ | 4-$C(CH_3)_3$ | 1 |
| $CH_2CH_3$ | 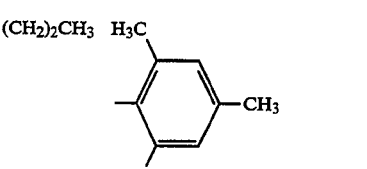 | $CH_2-CH_2-CH_2-C\equiv C-CH_2$ | — | 0 |
| $(CH_2)_2CH_3$ |  | $CH_2-CH_2-C\equiv C-CH_2-CH_2$ | — | 0 |

TABLE B-continued $$\text{structure: cyclohexenone with OH, R}^2\text{, =NOA-phenyl-(X)}_n\text{, R}^1\text{, =O}$$

| $R^1$ | $R^2$ | A | X | n |
|---|---|---|---|---|
| $CH_2CH_3$ | phenyl | $CH_2-C\equiv C-CH_2-CH_2-CH_2$ | $3\text{-}CF_3$ | 1 |
| $(CH_2)_2CH_3$ | phenyl | $CH_2-C\equiv C$ | $3\text{-}CF_3$ | 1 |
| $CH_2CH_3$ | phenyl | $CH_2-CH_2-C\equiv C$ | $4\text{-}C(CH_3)_3$ | 1 |
| $(CH_2)_2CH_3$ | phenyl | $CH_2-C\equiv C-CH_2$ | $4\text{-}C(CH_3)_3$ | 1 |
| $CH_2CH_3$ | phenyl | $CH_2-CH_2-CH_2-C\equiv C$ | — | 0 |
| $(CH_2)_2CH_3$ | phenyl | $CH_2-CH_2-C\equiv C$ | — | 0 |
| $CH_2CH_3$ | 4-CHO-phenyl | $CH_2-C\equiv C-CH_2$ | $3\text{-}CF_3$ | 1 |
| $(CH_2)_2CH_3$ | 4-(O-$CH_2$-C≡C)-phenyl | $CH_2-C\equiv C$ | $3\text{-}CF_3$ | 1 |
| $CH_2CH_3$ | 4-(NH-CO-$CH_3$)-phenyl | $CH_2-C\equiv C-CH_2$ | $4\text{-}C(CH_3)_3$ | 1 |
| $(CH_2)_2CH_3$ | 4-(NH-CO-$CH_3$)-2-F-phenyl | $CH_2-CH_2-C\equiv C$ | $4\text{-}C(CH_3)_3$ | 1 |

The cyclohexenone oxime ethers I are suitable as herbicides, in particular for controlling plant species from the family comprising the Graminaea (grasses).

The cyclohexenone oxime ethers I or the herbicides containing them can be applied, for example, in the form of directly sprayable solutions, powders, suspensions, including concentrated aqueous, oily or other suspensions or dispersions, emulsions, oil dispersions, pastes, dusting agents, broadcasting agents or granules, by spraying, atomizing, dusting, broadcasting or pouring. The application forms depend on the intended uses; they should in any case ensure very fine distribution of the novel active ingredients.

The compounds I are suitable in general for the preparation of directly sprayable solutions, emulsions, pastes or dispersions. Suitable inert additives are mineral oil fractions having a medium to high boiling point, such as kerosene or diesel oil, as well as coal tar oils and oils of vegetable or animal origin, aliphatic, cyclic and aromatic hydrocarbons, e.g. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by the addition of water. For the preparation of emulsions, pastes or oil dispersions, the substrates as such or dissolved in an oil or solvent can be homogenized in water by means of wetting agents, adherents, dispersants or emulsifiers. However, it is also possible to prepare concentrates which consist of active substance, wetting agents, adherents, dispersants or emulsifiers and possibly solvents or oil and which are suitable for dilution with water.

Suitable surfactants are alkali metal, alkaline earth metal and ammonium salts of aromatic sulfonic acids, for example lignin-, phenol-, naphthalene- or dibutylnaphthalenesulfonic acid, and of fatty acids, alkyl- and alkylarylsulfonates, alkylsulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or naphthalenesulfonic acids with phenol and formaldehyde, polyoxyethylene octylphenol ethers, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, broadcasting agents and dusting agents can be prepared by mixing or milling the active substances together with a solid carrier.

Granules, for example coated, impregnated and homogeneous granules, can be prepared by binding the active ingredients with solid carriers. Solid carriers are mineral earths, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flours, bark meal, wood meal and nutshell meal, cellulose powders or other solid carriers.

The formulations contain from 0.02 to 95, preferably from 0.5 to 90,% by weight of active ingredient. The active ingredients are used in a purity from 90 to 100%, preferably from 95 to 100% (according to the NMR spectrum).

The novel compounds I can be formulated, for example, as follows:

I. 90 parts by weight of compound No. 3.2 are mixed with 10 parts by weight of N-methyl-α-pyrrolidone, and a solution which is suitable for use in the form of very small drops is obtained.

II. 20 parts by weight of compound No. 3.4 are dissolved in a mixture which consists of 80 parts by weight of xylene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of compound No. 3.4 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and distributing it therein, an aqueous dispersion which contains 0.02% by weight of the active ingredient is obtained.

IV. 20 parts by weight of active ingredient No. 3.2 are dissolved in a mixture which consists of 25 parts by weight of cyclohexanone, 65 parts by weight of a mineral oil fraction boiling within a range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

V. 20 parts by weight of active ingredient No. 3.4 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 3.2 are mixed with 97 parts by weight of finely divided kaolin. A dusting agent which contains 3% by weight of the active ingredient is obtained in this manner.

VII. 30 parts by weight of active ingredient No. 3.4 are thoroughly mixed with a mixture of 92 parts by weight of silica gel powder and 8 parts by weight of liquid paraffin, which was sprayed onto the surface of the silica gel. A formulation of the active ingredient having good adhesion is obtained in this manner.

VIII. 20 parts by weight of active ingredient No. 3.2 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The agents can be applied by the preemergence or postemergence method. If the active ingredients are less well tolerated by certain crops, it is also possible to use application methods in which the herbicides are sprayed with the aid of the sprayers in such a way that the leaves of the sensitive crops are as far as possible not affected, whereas the active ingredients reach the leaves of undesirable plants growing underneath or the exposed soil surface (post-directed, lay-by).

The application rates of active ingredient are from 0.001 to 3, preferably from 0.01 to 2, kg/ha, depending on the season, the target plants and the stage of growth.

In view of the action spectrum for weed control, the toleration by crops and the desired influence on the growth of the latter and because of the wide range of application methods, the novel compounds can be used in a large number of crops. For example, the following crops are suitable:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris spp. altissima* | sugarbeets |
| *Beta vulgaris spp. rapa* | fodder beets |
| *Brassica napus var. napus* | rapeseed |
| *Brassica napus var. napobrassica* | swedes |
| *Brassica rapa var. silvestris* | beets |
| *Camellia sinesis* | tea plants |
| *Carthamus tinctorius* | safflower |
| *Carya illinoinensis* | pecan trees |
| *Citris limon* | lemons |
| *Citrus sinesis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elaeis guineensis* | oil palms |
| *Fragaria vesca* | strawberries |
| *Glycine max* | soybeans |
| *Gossypium hirsutum* (*Gossypium arboreum, Gossypium herbaceum, Gossypium vitifolium*) | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus spp.* | apple trees |
| *Manihot esculenta* | cassava |
| *Medicago sativa* | alfalfa (lucerne) |
| *Musa spp.* | banana plants |
| *Nicotiana tabacum* (*N. rustica*) | tobacco |
| *Olea europaea* | olive trees |
| *Oryza sativa* | rice |
| *Phaseolus lunatus* | limabeans |
| *Phaseolus vulgaris* | snapbeans, green beans, dry beans |
| *Picea abies* | Norway spruce |
| *Pinus spp.* | pine trees |
| *Pisum sativum* | English peas |
| *Prunus avium* | cherry trees |
| *Prunus persica* | peach trees |
| *Pyrus communis* | pear trees |
| *Ribes sylvestre* | redcurrants |
| *Ricinus communis* | casotr-oil plants |
| *Saccharum officinarum* | sugar cane |
| *Secale cereale* | rye |
| *Solanum tuberosum* | Irish potatoes |
| *Sorghum bicolor* (*s. vulgare*) | sorghum |
| *Theobroma cacao* | cacao plants |
| *Trifolium pratense* | red clover |
| *Triticum aestivum* | wheat |
| *Triticum durum* | duram wheat |
| *Vicia faba* | tick beans |
| *Vitis vinifera* | grape vines |
| *Zea mays* | Indian corn, sweet corn, maize |

To extend the action spectrum and to achieve synergistic effects, the cyclohexenone derivatives of the formula I can be mixed and applied with one another and with members of other groups of herbicidal or growth-regulating active ingredients. Examples of suitable components for the mixture are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, quinolinecarboxylic acids, cyclohexenones, (het)aryloxyphenoxypropionic acids, their salts, esters and amides, etc. derivatives of the formula I or herbicides containing them alone or in combination with other herbicides, or mixed with other crop protection agents, for example with pesticides or agents for controlling phytopathogenic fungi or bacteria. The miscibility with mineral salt solutions which are used for eliminating nutrient and trace element deficiencies is also of interest. It is also possible to add nonphytotoxic oils and oil concentrates.

The syntheses described below for the novel hydroxylamines can be used for obtaining further compounds of the formula III, with appropriate modification of the starting compounds. The compounds obtained are summarized in Tables 1 to 3.

PREPARATION EXAMPLES 4-(4-Fluorophenyl)-3-butynol (Example 1.1)

1 g of bis-(triphenylphosphine)-palladium(II) chloride, 3.8 g of copper(I) iodide and 8.7 g of triphenylphosphine were added in succession to a solution of 100 g of 4-bromofluorobenzene in 350 ml of triethylamine. This mixture was refluxed, after which 43.4 g of 3-butynol were added dropwise at this temperature (about 100° C.) in the course of 20 minutes. The mixture was stirred for a further 5 hours at this temperature. After the mixture had cooled, the triethylamine was distilled off. The residue was taken up in methyl tert-butyl ether and water. The aqueous phase was extracted twice with methyl tert-butyl ether, and the combined organic extracts were washed in succession with 1 N hydrochloric acid and with 10% strength sodium bicarbonate solution, dried over sodium sulfate and evaporated down in a rotary evaporator. Distillation under greatly reduced pressure gave 80 g (86%) of the desired compound.

5-Aminooxy-1-(4-fluorophenyl)-1-pentyne (Example 2.6)

N-(5-(4-Fluorophenyl)-4-pentynyloxy)-phthalimide (Example 1.10)

33.4 g (0,205 mol) of N-hydroxyphthalimide and 53.8 g (0.205 mol) of triphenylphosphine were added to a solution of 33.1 g (0.186 mol) of 5-hydroxy-1-(4-fluorophenyl)-1-pentyne in 430 ml of dry tetrahydrofuran. 35.7 g (0.205 mol) of diethyl azodicarboxylate were then added dropwise in the course of 2.5 hours with temperature control (max. 40° C.). Stirring was carried out overnight at room temperature, the mixture was evaporated down under reduced pressure and the residue was taken up with 300 ml of dichloromethane. The solution was washed twice with sodium carbonate solution and once with saturated sodium chloride solution. After drying and evaporating down, the crude product was purified by chromatography over silica gel. The eluent used was initially dichloromethane/n-hexane and subsequently pure dichloromethane.

Yield: 49 g (82%); mp. 87°–88° C. 250-MHz-$^1$H-NMR (DMSO-d6): δ(ppm)=1.9–2.1 (m, 2H); 2.68 (t, 2H); 4.32 (t, 2H); 7.18 (t, 2H); 7.4–7.6 (m, 2H); 7.85 (s, 4H).

5-Aminooxy-1-(4-fluorophenyl)-1-pentyne (Example 2.6)

47.7 g (0.148 mol) of the phthalimidoether prepared above were added a little at a time to a mixture of 68 ml of ethanolamine and 40 ml of dichloromethane. After the mixture had been stirred for 2 hours at room temperature, a clear solution had formed. The latter was added to 300 ml of ice-cold, saturated sodium chloride solution. The mixture was extracted three times with 100 ml of dichloromethane, and the combined organic phases were washed once with sodium chloride solution, dried and evaporated down. The title compound was obtained as an oil.

Yield: 27.1 g (95%) 250 -MHz-$^1$H-NMR (CDCl$_3$): δ(ppm)=1.8–2.0 (m, 2H); 2.47 (t, 2H); 3.8 (t, 2H); 5.4 (broad s, 2H); 6.9–7.1 (m, 2H); 7.3–7.45 (m, 2H).

1-Aminooxy-4-phenyl-2-butyne (Example 2.2)

1-Bromo-4-phenyl-2-butyne (Example 1.8)

14.5 ml of pyridine were added to a mixture of 140.4 g (0.96 mol) of 4-phenyl-2-butyn-1-ol (prepared according to G. Dupont, Bull. Soc. Chim. Fr., 1954, page 816) and 600 ml of dry toluene, after which 119.1 g (0.44 mol) of phosphorus tribromide were added dropwise in the course of 2 hours, the temperature not being allowed to exceed 50° C. The mixture was stirred overnight at room temperature and then poured onto 1,000 ml of ice water, the organic phase was separated off and the aqueous phase was extracted several times with methyl tert-butyl ether. The combined organic phases were then washed neutral and dried. The crude product obtained after the solvent had been stripped off under reduced pressure was subjected to fractional distillation. Yield: 126 g of product having a purity of 93% according to gas chromatography; bp.: 83°–85° C. at 0.3 mbar.

N-(4-Phenyl-2-butynyloxy)-phthalimide (Example 1.9)

51.3 g (0.23 mol) of the 1-bromo-4-phenyl-2-butyne obtained above were added dropwise in the course of 30 minutes to a mixture consisting of 230 ml of N-methyl-pyrrolid-2-one, 3 g of potassium iodide, 37 g (0.23 mol) of N-hydroxyphthalimide and 20.6 g (0.15 mol) of potassium carbonate. Stirring was carried out for a further 5 hours at 60° C. and then overnight at room temperature, the mixture was poured into 800 ml of ice water and the precipitated crystals were filtered off under suction and washed thoroughly with water and isopropanol.

Yield: 57 g (86%); mp.: 127°–129° C. 250-MHz-$^1$H-NMR (DMSO-d6) δ(ppm)=3.71 (t, 2H); 4.95 (t, 2H); 7.28 (s, 5H); 7.9 (s, 4H)

1-Aminooxy-4-phenyl-2-butyne (Example 2.2)

6 g (0.099 mol) of ethanolamine were added dropwise to a solution of 28.7 g (0.099 mol) of the phthalimidoether prepared above, in 100 ml of ethyl acetate. Stirring was carried out for 1.5 hours at 30° C., the mixture was cooled in an ice bath, the crystals were filtered off under suction and a solution of 8.9 g (0.099 mol) of oxalic acid in 130 ml of ethyl acetate was added to the mother liquor. The title compound was obtained as the oxalate. The crystals were filtered off under suction, washed with cold ethyl acetate and dried under reduced pressure.

Yield: 20.2 g (81%); mp. 113°–117° C. 300 MHz-$^1$H-NMR ( DMSO-d6 ) δ(ppm)=3.7 (s, 2H); 4.39 (s, 2H); 7.2–7.4 (m, 5H); 10.5 (broad s)

TABLE 1

| | X-A-Z | | | |
|---|---|---|---|---|
| | X-A | Z | | Phys. data X$^1$H-NMR/mp. [°C.]/bp. [°C./mbar] |
| 1.1 | X—CH$_2$—CH$_2$—C≡C | 4-F-phenyl | OH | 2.65(t,2H);3.8(t,2H);6.95(t,2H) |
| 1.2 | X—CH$_2$—CH$_2$—C≡C | 4-Cl-phenyl | OH | 2.65(t,2H);3.8(t,2H);7.35(d,2H) |
| 1.3 | X—CH$_2$—CH$_2$—C≡C | Pyridin-3-yl | OH | 2.65(t,2H);3.8(t,2H);8.45(d,1H) |
| 1.4 | X—CH$_2$—CH$_2$—CH$_2$—C≡C | 4-F-phenyl | OH | 1.85(m,2H);2.5(t,2H);6.95(t,2H) |
| 1.5 | X—CH$_2$—CH$_2$—CH$_2$—C≡C | 4-Cl-phenyl | OH | 1.80(m,2H);2.5(t,2H);7.35(d,2H) |
| 1.6 | X—CH$_2$—C≡C—CH$_2$ | 4-Cl-phenyl | Br | |
| 1.7 | X—CH$_2$—C≡C—CH$_2$ | 4-F-phenyl | Br | |
| 1.8 | X—CH$_2$—C≡C—CH$_2$ | 4-Phenyl | Br | 83–85/0.3 |
| 1.9 | X—CH$_2$—C≡C—CH$_2$ | 4-Phenyl | M | 127–129 |
| 1.10 | X—CH$_2$—CH$_2$—C≡C | 4-F-phenyl | M | 87–88 |
| 1.11 | X—CH$_2$—CH$_2$—C≡C | 4-Cl-phenyl | M | |
| 1.12 | X—CH$_2$—CH$_2$—C≡C | Pyridin-3-yl | M | |
| 1.13 | X—CH$_2$—CH$_2$—CH$_2$—C≡C | 4-F-phenyl | M | |
| 1.14 | X—CH$_2$—CH$_2$—CH$_2$—C≡C | 4-Cl-phenyl | M | |
| 1.15 | X—CH$_2$—C≡C—CH$_2$ | 4-Cl-phenyl | M | |
| 1.16 | X—CH$_2$—C≡C—CH$_2$ | 4-F-phenyl | M | |
| 1.17 | X—CH$_2$—CH=C(CH$_3$)—C≡C—*) | 4-Cl-phenyl | M | 109–111 |
| 1.18 | X—CH$_2$—CH=C(CH$_3$)—C≡C—*) | 4-F-phenyl | M | |
| 1.19 | X—CH$_2$—CH=C(CH$_3$)—C≡C—*) | 4-F-phenyl | OH | |
| 1.20 | X—CH$_2$—CH=C(CH$_3$)—C≡C—*) | 4-Cl-phenyl | OH | |

M =
*)Z-configuration about the double bond

TABLE 2

| | H$_2$N-O-A-Z | | Phys. data |
|---|---|---|---|
| | O-A | Z | $^1$H-NMR/mp. [°C.] |
| 2.1 | —O—CH$_2$—C≡C— | Phenyl | |
| 2.2 | —O—CH$_2$—C≡C—CH$_2$— | Phenyl | 113–117 |
| 2.3 | —O—CH$_2$—CH$_2$—C≡C— | 4-F-phenyl | 2.7(t);3.86(t);5.5(s);6.9–7.05(m);7.3–7.45(m) |
| 2.4 | —O—CH$_2$—CH$_2$—C≡C— | 4-Cl-phenyl | |
| 2.5 | —O—CH$_2$—CH$_2$—C≡C— | Pyridin-3-yl | |
| 2.6 | —O—CH$_2$—CH$_2$—CH$_2$—C≡C— | 4-F-phenyl | 2.47(t);3.8(t);5.4(s);6.9–7.1(m);7.3–7.45(m) |

TABLE 2-continued

| H₂N-O-A-Z | | Phys. data |
|---|---|---|
| O-A | Z | ¹H-NMR/mp. [°C.] |
| 2.7 —O—CH₂—CH₂—CH₂—C≡C— | 4-Cl-phenyl | |
| 2.8 —O—CH₂—C≡C—CH₂— | 4-Cl-phenyl | |
| 2.9 —O—CH₂—C≡C—CH₂— | 4-F-phenyl | |
| 2.10 —O—CH₂—CH=C(CH₃)—C≡C—*) | 4-F-phenyl | |
| 2.11 —O—CH₂—CH=C(CH₃)—C≡C—*) | 4-Cl-phenyl | |
| 2.12 —C—CH₂—CH=C(CH₃)—C≡C—**) | 4-F-phenyl | |
| 2.13 —O—CH₂—CH=C(CH₃)—C≡C—**) | 4-Cl-phenyl | 54–56 |

*)E-configuration about the double bond
**)Z-configuration about the double bond The method described in the Synthesis Example below was used for obtaining further compounds of the formula I, with appropriate modification of the starting compounds; the compounds obtained are listed in the Tables below, together with physical data; compounds without these data can be synthesized from the corresponding substances in a similar manner. Because of their close structural relationships with the compounds prepared and investigated, they are expected to have a similar action.

Preparation Method for 2-[1-(4-(4-fluorophenyl)-but-3-ynyloximino)-butyl]-3-hydroxy-5-tetrahydropyran-4-ylcyclohex-2-enone (Example 3.20)

2.7 g (15 mmol) of 4-(4-fluorophenyl)-but-3-ynoxyamine were added to a solution of 4 g (15 mmol) of 2-butyryl-3-hydroxy-5-tetrahydropyran-4-ylcyclohex-2-enone in 60 ml of dry methanol. After the mixture had been stirred for 16 hours at room temperature, the methanol was removed under reduced pressure from a water pump. The crude product was purified by chromatography over silica gel (eluent: methylene chloride).
Yield: 5.2 g (81.2%).

TABLE 3

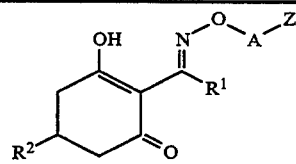

| Compound no | R² | R¹ | O—A | Z | ¹H-NMR*) [δ ppm] | mp. [°C.] |
|---|---|---|---|---|---|---|
| 3.1 | Tetrahydrothiopyran-3-yl | Propyl | —O—CH₂—C≡C— | Phenyl | 4.9(s, 2H); 7.2–7.6(m, 5H) | |
| 3.2 | Tetrahydrothiopyran-3-yl | Propyl | —O—CH₂—C≡C—CH₂— | Phenyl | 3.6(s, 2H); 4.7(s, 2H), 7.2–7.5 (m, 5H) | |
| 3.3 | Tetrahydrothiopyran-3-yl | Ethyl | —O—CH₂—C≡C—CH₂— | Phenyl | 3.65(s, 2H); 4.7(s, 2H); 7.2–7.5(m, 5H) | |
| 3.4 | Tetrahydropyran-3-yl | Propyl | —O—CH₂—C≡C—CH₂— | Phenyl | 3.65(s, 2H); 4.7(s, 2H); 7.2–7.5(m, 5H) | |
| 3.5 | 2-Ethylthiopropyl | Propyl | —O—CH₂—C≡C— | Phenyl | 4.9(s, 2H); 7.3–7.6(m, 5H) | |
| 3.6 | 2-Ethylthiopropyl | Propyl | —O—CH₂—C≡C—CH₂— | Phenyl | 3.65(s, 2H); 4.7(s, 2H); 7.2–7.5(m, 5H) | |
| 3.7 | Tetrahydropyran-4-yl | Ethyl | —O—CH₂—C≡C—CH₂— | Phenyl | 3.65(s, 2H); 4.7(s, 2H); 7.2–7.5(m, 5H) | |
| 3.8 | Tetrahydropyran-4-yl | Propyl | —O—CH₂—C≡C—CH₂— | Phenyl | 3.6(s, 2H); 4.65(s, 2H); 7.1–7.6(m, 5H) | |
| 3.9 | Tetrahydropyran-4-yl | Propyl | —O—(CH₂)₃—C≡C— | 4-F-phenyl | 4.25(t, 2H); 6.8–7.5(2m, 4H) | |
| 3.10 | Tetrahydropyran-4-yl | Ethyl | —O—(CH₂)₃—C≡C— | 4-F-phenyl | 4.25(t, 2H); 6.8–7.5(2m, 4H) | |
| 3.11 | Tetrahydrothiopyran-3-yl | Ethyl | —O—(CH₂)₃—C≡C— | 4-F-phenyl | 4.25(t, 2H); 6.8–7.5(2m, 4H) | |
| 3.12 | Tetrahydrothiopyran-3-yl | Propyl | —O—(CH₂)₃—C≡C— | 4-F-phenyl | 4.25(t, 2H); 6.8–7.5(2m, 4H) | |
| 3.13 | Tetrahydropyran-3-yl | Ethyl | —O—(CH₂)₃—C≡C— | 4-F-phenyl | 4.25(t, 2H); 6.8–7.5(2m, 4H) | |
| 3.14 | Tetrahydropyran-3-yl | Propyl | —O—(CH₂)₃—C≡C— | 4-F-phenyl | 4.25(t, 2H); 6.8–7.5(2m, 4H) | |
| 3.15 | Tetrahydrothiopyran-3-yl | Ethyl | —O—CH₂—CH₂—C≡C— | 4-F-phenyl | 4.25(t); 6.98(dd); 7.35(dd) | 74–90 |
| 3.16 | Tetrahydrothiopyran-3-yl | Propyl | —O—CH₂—CH₂—C≡C— | 4-F-phenyl | 4.25(t); 6.98(dd); 7.35(dd) | — |

TABLE 3-continued

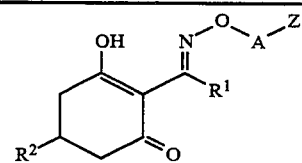

| Compound no | R² | R¹ | O—A | Z | ¹H-NMR*) [δ ppm] | mp. [°C.] |
|---|---|---|---|---|---|---|
| 3.17 | Tetrahydropyran-3-yl | Ethyl | —O—CH₂—CH₂—C≡C— | 4-F-phenyl | 4.25(t); 6.98(dd); 7.35(dd) | 55–61 |
| 3.18 | Tetrahydropyran-3-yl | Propyl | —O—CH₂—CH₂—C≡C— | 4-F-phenyl | 4.25(t); 6.98(dd); 7.35(dd) | — |
| 3.19 | Tetrahydropyran-4-yl | Ethyl | —O—CH₂—CH₂—C≡C— | 4-F-phenyl | 4.25(t); 6.98(dd); 7.35(dd) | 83–87 |
| 3.20 | Tetrahydropyran-4-yl | Propyl | —O—CH₂—CH₂—C≡C— | 4-F-phenyl | 4.25(t); 6.98(dd); 7.35(dd) | 98–102 |
| 3.21 | 3-Isopropylisoxazol-5-yl | Propyl | —O—CH₂—CH₂—C≡C— | 4-F-phenyl | 4.25(t); 5.94(s); 7.0(dd); 7.37(dd) | — |
| 3.22 | 4-Methylphenyl | Propyl | —O—CH₂—CH₂—C≡C— | 4-F-phenyl | 4.25(t); 6.98(dd); 7.15(m); 7.35(dd) | 65–69 |
| 3.23 | 3,4-Dibromotetrahydropyran-3-yl | Propyl | —O—CH₂—CH₂—C≡C— | 4-F-phenyl | 4.25(t); 6.98(dd); 7.35(dd) | — |
| 3.24 | Tetrahydrothiopyran-3-yl | Propyl | —O—CH₂—CH₂—C≡C— | 4-Cl-phenyl | 4.25(t); 7.25(d); 7.35(d) | — |
| 3.25 | Tetrahydrothiopyran-3-yl | Ethyl | —O—CH₂—CH₂—C≡C— | 4-Cl-phenyl | 4.25(t); 7.25(d); 7.35(d) | 82–86 |
| 3.26 | Tetrahydropyran-3-yl | Ethyl | —O—CH₂—CH₂—C≡C— | 4-Cl-phenyl | 4.25(t); 7.25(d); 7.35(d) | 99–101 |
| 3.27 | Tetrahydropyran-3-yl | Propyl | —O—CH₂—CH₂—C≡C— | 4-Cl-phenyl | 4.25(t); 7.25(d); 7.35(d) | — |
| 3.28 | Tetrahydropyran-4-yl | Ethyl | —O—CH₂—CH₂—C≡C— | 4-Cl-phenyl | 4.25(t); 7.25(d); 7.35(d) | 98–101 |
| 3.29 | Tetrahydropyran-4-yl | Propyl | —O—CH₂—CH₂—C≡C— | 4-Cl-phenyl | 4.25(t); 7.25(d); 7.35(d) | 115–118 |
| 3.30 | Isopropylisoxazol-5-yl | Propyl | —O—CH₂—CH₂—C≡C— | 4-Cl-phenyl | 4.25(t); 5.9(s); 7.25(d); 7.35(d) | 71–74 |
| 3.31 | 4-Methylphenyl | Propyl | —O—CH₂—CH₂—C≡C— | 4-Cl-phenyl | 4.25(t); 7.45(m); 7.28(M) | 93–6 |
| 3.32 | 3,4-Dibromotetrahydropyran-3-yl | Propyl | —O—CH₂—CH₂—C≡C— | 4-Cl-phenyl | 4.25(t); 7.25(d); 7.25(d) | — |
| 3.33 | Tetrahydrothiopyran-3-yl | Ethyl | —O—(CH₂)₃—C≡C— | 4-Cl-phenyl | 1.15(t); 4.2(t); 7.25(d); 7.35(d) | |
| 3.34 | Tetrahydrothiopyran-3-yl | Propyl | —O—(CH₂)₃—C≡C— | 4-Cl-phenyl | 0.98(t); 4.2(t); 7.25(d); 7.35(d) | |
| 3.35 | Tetrahydropyran-3-yl | Ethyl | —O—(CH₂)₃—C≡C— | 4-Cl-phenyl | 1.15(t); 4.2(t); 7.25(d); 7.35(d) | |
| 3.36 | Tetrahydropyran-3-yl | Propyl | —O—(CH₂)₃—C≡C— | 4-Cl-phenyl | 0.95(t); 4.2(t); 7.25(d); 7.35(d) | |
| 3.37 | Tetrahydropyran-4-yl | Ethyl | —O—(CH₂)₃—C≡C— | 4-Cl-phenyl | 1.15(t); 4.2(t); 7.25(d); 7.35(d) | |
| 3.38 | Tetrahydropyran-4-yl | Propyl | —O—(CH₂)₃—C≡C— | 4-Cl-phenyl | 0.98(t); 4.2(t); 7.25(d); 7.35(d) | |
| 3.39 | Tetrahydrothiopyran-3-yl | Ethyl | —O—CH₂—CH₂—C≡C— | 2-Thienyl | 1.15(t); 2.75(t); 4.25(t); 7.05(m); 7.2(m) | |
| 3.40 | Tetrahydrothiopyran-3-yl | Propyl | —O—CH₂—CH₂—C≡C— | 2-Thienyl | 0.95(t); 2.75(t); 4.25(t); 7.05(m); 7.2(m) | |
| 3.41 | Tetrahydropyran-3-yl | Ethyl | —O—CH₂—CH₂—C≡C— | 2-Thienyl | 1.15(t); 2.75(t); 4.25(t); 7.05(m); 7.2(m) | |
| 3.42 | Tetrahydropyran-3-yl | Propyl | —O—CH₂—CH₂—C≡C— | 2-Thienyl | 0.95(t); 2.75(t); 4.25(t); 7.05(m); 7.2(m) | |
| 3.43 | Tetrahydropyran-4-yl | Ethyl | —O—CH₂—CH₂—C≡C— | 2-Thienyl | 1.15(t); 2.75(t); 4.25(t); 7.05(m); 7.2(m) | |
| 3.44 | Tetrahydropyran-4-yl | Propyl | —O—CH₂—CH₂—C≡C— | 2-Thienyl | 0.95(t); 2.75(t); 4.25(t); 7.05(m); 7.2(m) | |

*)selected signals

USE EXAMPLES

The action of the cyclohexenone derivatives of the formula I on plant growth can be demonstrated by greenhouse experiments:

The culture vessels used were plastic flower pots containing loamy sand with about 3.0% of humus as a substrate. The seeds of the test plants were sown separately according to species.

In the preemergence treatment, the active ingredients suspended or emulsified in water were applied directly after sowing, by means of finely distributing nozzles. The vessels were lightly watered in order to promote germination and growth and were then covered with transparent plastic covers until the plants had begun to grow. This covering ensures uniform germination of the test plants, unless this has been adversely affected by the active ingredients.

For the postemergence treatment, the test plants were treated with the active ingredients suspended or emulsified in water, this being carried out only at a height of growth of from 3 to 15 cm, depending on the form of growth. The application rate for the postemergence treatment was 0.25 kg/ha of active ingredient.

The plants were kept at 10°–25° C. or 20°–35° C., according to the species. The test period extended over 2 to 4 weeks. During this time, the plants were tended and their reaction to the individual treatments was evaluated.

Evaluation was based on a scale from 0 to 100. 100 means no emergence of the plants or complete destruction of at least the above-ground parts and 0 means no damage or normal growth.

The plants used in the greenhouse experiments consisted of the following species:

| Botanical name | Common name |
| --- | --- |
| Echinochloa crus-galli | barnyard grass |
| Oryza sativa | rice |
| Setaria italica | foxtail millet |
| Setaria viridis | green foxtail |

When 0.25 kg/ha of active ingredient is used in the postemergence method, undesirable grass-like plants are very well controlled by compounds No. 3.2 and 3.4, which are also well tolerated by the example crop rice.

We claim:

1. A cyclohexenone oxima ether of the formula I

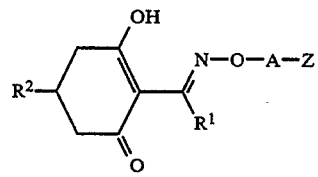

where
R$^1$ is C$_1$–C$_6$-alkyl;
A is a C$_3$–C$_6$-alkynylene chain which is unsubstituted or substituted by 1 to 3 C$_1$–C$_3$-alkyl groups or halogen atoms;
Z is phenyl which is unsubstituted or substituted by n identical or different radicals X, and R$^2$ means a C$_1$–C$_6$-alkyl or C$_3$–C$_6$-cycloalkyl group, both substituted by C$_1$–C$_4$-alkylthio, or a phenyl group which is unsubstituted or substituted by one to three radicals selected from the group consisting of halogen, nitro, cyano, C$_1$–C$_4$-alkyl, C$_1$–C$_4$-alkoxy, C$_1$–C$_4$-alkylthio, C$_1$–C$_4$-haloalkyl, C$_3$–C$_6$-alkenyloxy and C$_3$–C$_6$-alkynyloxy;
X is nitro, cyano, halogen, C$_1$–C$_4$-alkyl, C$_1$–C$_4$-alkoxy, C$_1$–C$_4$-alkylthio, C$_1$–C$_4$-haloalkyl, C$_1$–C$_4$-haloalkoxy, carboxyl, C$_1$–C$_4$-alkoxycarbonyl, benzyloxycarbonyl or phenyl, where the aromatic radicals may carry one to three substituents selected from the group consisting of nitro cyano, halogen, C$_1$–C$_4$-alkyl, C$_1$–C$_4$-alkoxy, C$_1$–C$_4$-alkylthio, C$_1$–C$_4$-haloalkyl, C$_1$–C$_4$-haloalkoxy, carboxyl, C$_1$–C$_4$alkoxycarbonyl and benzyloxycarbonyl;
n is from 0 to 3, or from 1 to 5 where X is halogen;
and its agriculturally useful salts and esters of C$_1$–C$_{10}$-carboxylic acids and inorganic acids.

2. A herbicide containing inert additives and a herbicidal amount of one or more compounds of the formula I as claimed in claim 1.

3. A method for controlling undesirable plant growth, wherein the undesirable plants or their habitat is or are treated with a herbicidal amount of a cyclohexenone derivative of the formula I as claimed in claim 1.

* * * * *

UNITED STATES PATENT AND TRADEMARK OFFICE
CERTIFICATE OF CORRECTION

PATENT NO.: 5,374,609

DATED: December 20, 1994

INVENTOR(S): KAST et al.

It is certified that error appears in the above-identified patent and that said Letters Patent is hereby corrected as shown below:

Column 46, claim 1, line 30, "$C_{1-C4}$" should be -- $C_1$-$C_4$- --.

Column 46, claim 1, line 32, "$C_{1-C4}$" should be -- $C_1$-$C_4$- --.

Signed and Sealed this

Second Day of May, 1995

*Attest:*

BRUCE LEHMAN

*Attesting Officer*  *Commissioner of Patents and Trademarks*